(12) United States Patent
Freitag et al.

(10) Patent No.: US 8,093,320 B2
(45) Date of Patent: *Jan. 10, 2012

(54) COMPOSITIONS COMPRISING POLYPHOSPHONATES AND ADDITIVES THAT EXHIBIT AN ADVANTAGEOUS COMBINATION OF PROPERTIES, AND METHODS RELATED THERETO

(75) Inventors: Dieter Freitag, Chelmsford, MA (US); Pin Go, Lowell, MA (US); Gad Stahl, Kibbutz Kfar-Aza (IL)

(73) Assignee: FRX Polymers, Inc., Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/699,376

(22) Filed: Feb. 3, 2010

(65) Prior Publication Data
US 2010/0204354 A1    Aug. 12, 2010

Related U.S. Application Data

(63) Continuation of application No. 11/549,789, filed on Oct. 16, 2006, now Pat. No. 7,666,932.

(60) Provisional application No. 60/727,466, filed on Oct. 17, 2005.

(51) Int. Cl.
| | |
|---|---|
| *C08G 18/77* | (2006.01) |
| *C08K 5/34* | (2006.01) |
| *C08K 5/15* | (2006.01) |
| *C08K 5/00* | (2006.01) |
| *C08K 5/13* | (2006.01) |
| *C07F 9/6574* | (2006.01) |
| *C07F 9/40* | (2006.01) |
| *C07C 37/20* | (2006.01) |
| *C08F 110/00* | (2006.01) |
| *C08F 14/00* | (2006.01) |
| *A61F 13/15* | (2006.01) |

(52) U.S. Cl. ........ 524/115; 524/101; 524/110; 524/117; 524/131; 524/291; 524/343; 524/344; 524/349; 521/143; 521/146; 521/149; 521/282; 521/155

(58) Field of Classification Search ............... 521/143, 521/146, 149, 155, 182; 524/101, 110, 115, 524/117, 131, 291, 343, 344, 349
See application file for complete search history.

(56) References Cited

U.S. PATENT DOCUMENTS

| | | | |
|---|---|---|---|
| 2,534,242 A | 12/1940 | Cusie | |
| 2,435,252 A | 2/1948 | Toy | |
| 2,682,522 A | 6/1954 | Coover et al. | |
| 2,716,101 A | 8/1955 | Coover et al. | |
| 2,891,915 A | 6/1959 | McCormack et al. | |
| 3,153,008 A | 10/1964 | Fox | |
| 3,271,329 A | 9/1966 | Coover, Jr. et al. | |
| 3,326,852 A | 6/1967 | Thomas et al. | |
| 3,442,854 A | 5/1969 | Curtius et al. | |
| 3,719,727 A | 3/1973 | Masai et al. | |
| 3,829,405 A | 8/1974 | Cohen et al. | |
| 3,830,771 A | 8/1974 | Cohen et al. | |
| 3,919,363 A | 11/1975 | Ura et al. | |
| 3,925,303 A | 12/1975 | Rio et al. | |
| 3,932,351 A | 1/1976 | King | |
| 3,932,566 A | 1/1976 | Reader | |
| 3,946,093 A | 3/1976 | Koto et al. | |
| 3,952,072 A | 4/1976 | Yonemitsu et al. | |
| 4,033,927 A | 7/1977 | Borman | |
| 4,048,106 A | 9/1977 | Hermans | |
| 4,064,107 A | 12/1977 | Stackman et al. | |
| 4,078,016 A | 3/1978 | Kramer | |
| 4,093,582 A | 6/1978 | Mark et al. | |
| 4,152,373 A | 5/1979 | Honig et al. | |
| 4,223,104 A | 9/1980 | Kim et al. | |
| 4,229,552 A | 10/1980 | Shiozaki et al. | |
| 4,254,177 A | 3/1981 | Fulmer | |
| 4,258,153 A | 3/1981 | Yomamoto et al. | |
| 4,322,520 A | 3/1982 | Schmidt et al. | |
| 4,322,530 A | 3/1982 | Jachimowicz | |
| 4,328,174 A | 5/1982 | Schmidt et al. | |
| 4,331,614 A | 5/1982 | Schmidt et al. | |
| 4,332,921 A | 6/1982 | Schmidt et al. | |
| 4,350,793 A | 9/1982 | Schmidt et al. | |
| 4,374,971 A | 2/1983 | Schmidt et al. | |
| 4,377,537 A | 3/1983 | Block et al. | |
| 4,401,802 A | 8/1983 | Schmidt et al. | |
| 4,408,033 A | 10/1983 | Hefner, Jr. | |
| 4,415,719 A | 11/1983 | Schmidt et al. | |

(Continued)

FOREIGN PATENT DOCUMENTS
EP    0077493 B1    3/1987
(Continued)

OTHER PUBLICATIONS

Billmeyer, Textbook of Polymer Science, $2^{nd}$ Ed., *Wiley Interscience*, New York (1971), 45-52.
Cotter, Engineering Plastics: A Handbook of Polyarylethers, *Science Publ. S.A.*, Switzerland (1995), TOC (Gordon and Breach Publishers).
Groggins, Unit Processes in Organic Synthesis, $4^{th}$ Ed., *McGraw-Hill Book Company, Inc.* (1952), 616-620.

(Continued)

*Primary Examiner* — Timothy J. Kugel
*Assistant Examiner* — Atnaf Admasu
(74) *Attorney, Agent, or Firm* — Pepper Hamilton LLP

(57) ABSTRACT

Disclosed are new compositions consisting of polyphosphonates and specific additive compositions that exhibit superior resistance to degradation due to exposure to air, high temperature and air, moisture or combinations thereof. Also disclosed are polymer mixtures or blends comprising these polyphosphonates/additive compositions and commodity and engineering plastics and articles produced therefrom. Further disclosed are articles of manufacture produced from these materials, such as fibers, films, coated substrates, moldings, foams, fiber-reinforced articles, or any combination thereof.

15 Claims, No Drawings

U.S. PATENT DOCUMENTS

| | | | |
|---|---|---|---|
| 4,474,937 A | 10/1984 | Bales | |
| 4,481,350 A | 11/1984 | Schmidt et al. | |
| 4,508,890 A | 4/1985 | Schmidt et al. | |
| 4,594,404 A | 6/1986 | Kawakami et al. | |
| 4,719,279 A | 1/1988 | Kauth et al. | |
| 4,762,905 A | 8/1988 | Schmidt et al. | |
| 4,782,123 A | 11/1988 | Kauth et al. | |
| 4,788,259 A | 11/1988 | Nielinger et al. | |
| 5,003,029 A | 3/1991 | Ueda et al. | |
| 5,034,056 A | 7/1991 | Von Bonin | |
| 5,039,775 A | 8/1991 | Oyaizu | |
| 5,086,153 A | 2/1992 | Oyaizu | |
| 5,216,113 A | 6/1993 | Schulz-Schlitte et al. | |
| 5,256,714 A | 10/1993 | Liu et al. | |
| 5,319,058 A | 6/1994 | Hattori et al. | |
| 5,334,692 A | 8/1994 | Hess et al. | |
| 5,334,694 A | 8/1994 | Jung et al. | |
| 5,362,783 A | 11/1994 | Eiffler et al. | |
| 5,525,681 A | 6/1996 | Barron et al. | |
| 5,639,800 A | 6/1997 | Von Bonin et al. | |
| 5,719,200 A | 2/1998 | Staendeke et al. | |
| 5,919,844 A | 7/1999 | Shimizu et al. | |
| 6,066,700 A | 5/2000 | König et al. | |
| 6,288,210 B1 | 9/2001 | Shobha et al. | |
| 6,291,630 B1 | 9/2001 | König et al. | |
| 6,861,499 B2 | 3/2005 | Vinciguerra et al. | |
| 6,872,797 B2 | 3/2005 | Ueno et al. | |
| 7,666,932 B2 | 2/2010 | Freitag et al. | |
| 2004/0167284 A1 | 8/2004 | Vinciguerra et al. | |
| 2005/0020800 A1 | 1/2005 | Levchik et al. | |
| 2005/0222370 A1 | 10/2005 | Freitag et al. | |
| 2006/0020104 A1 | 1/2006 | Freitag | |

FOREIGN PATENT DOCUMENTS

| | | | |
|---|---|---|---|
| EP | 0 383 978 | * | 8/1990 |
| EP | 1026191 A1 | | 8/2000 |
| GB | 2043083 A | | 10/1980 |
| WO | WO99/46315 | | 9/1999 |
| WO | WO03/029258 A1 | | 4/2003 |
| WO | WO2004/076536 A1 | | 9/2004 |
| WO | WO2004/076537 A1 | | 9/2004 |

OTHER PUBLICATIONS

Legrand, et al., 'Handbook of Polycarbonate Science and Technology, *Marcel Dekker, Inc.*, New York (2000), TOC.

Levchik, et al., Overview of recent developments in the flame retardancy of polycarbonates, *Polym Int* (Mar. 22, 1995), 54:981-998.

Morgan, Condensation Polymers: By Interfacial and Solution Methods, *Interscience Publishers*, New York, (1965), 217-223.

Schmidt, et al., Aromatische Polyphosphonate: Thermoplastisehe Polymere von extremer Brandwidrigkeit, *Die Angewadte Makromolekulare Chemie* (1985) 132(Nr.165):1-18.

Polymeric Materials Encyclopedia, vol. 1, Editor-in-Chief Joseph C. Salamone, pp. 316-320, by CRC Press, 1996.

* cited by examiner

COMPOSITIONS COMPRISING POLYPHOSPHONATES AND ADDITIVES THAT EXHIBIT AN ADVANTAGEOUS COMBINATION OF PROPERTIES, AND METHODS RELATED THERETO

RELATED APPLICATIONS

This application is a continuation of U.S. patent application Ser. No. 11/549,789, filed Oct. 16, 2006, now U.S. Pat. No. 7,666,932, issued Feb. 23, 2010, which claims priority to U.S. Provisional Application No. 60/727,466 filed Oct. 17, 2005 titled "COMPOSITIONS COMPRISING POLYPHOSPHONATES AND ADDITIVES THAT EXHIBIT AN ADVANTAGEOUS COMBINATION OF PROPERTIES, AND METHODS RELATED THERETO", the contents of which are incorporated hereby by reference.

TECHNICAL FIELD

The present invention relates generally to new compositions consisting of polyphosphonates and specific additive compositions that exhibit superior resistance to degradation due to exposure to air, high temperature and air, moisture or combinations thereof. It also relates to polymer mixtures or blends comprising these polyphosphonates/additive compositions, and flame retardant coatings and articles produced therefrom.

BACKGROUND

The production of linear, aromatic polyphosphonates by condensing aryl phosphonic acid dichlorides and aromatic diols in a solvent in the absence of a catalyst or in the presence of alkaline-earth metal halide catalysts is a known process and is described in several U.S. patents (see e.g., U.S. Pat. Nos. 2,534,252; 3,946,093; 3,919,363 and 6,288,210 B1). The polyphosphonates are isolated from the solutions by precipitation into methanol or by evaporation of the solvent. Polyphosphonates are known to exhibit excellent fire resistance (see e.g., U.S. Pat. Nos. 2,682,522, 2,891,915 and 4,331,614). It is known (see e.g., U.S. Pat. No. 2,682,522) that linear polyphosphonates can be produced by melt condensing a phosphonic acid diaryl ester and a bisphenol using a metal catalyst (e.g., sodium phenolate) at high temperature. This approach produced low molecular weight polyphosphonates that exhibited poor toughness.

Consequently, to improve toughness a synthetic approach to produce branched polyphosphonates by the transesterification process was developed (see e.g., U.S. Pat. No. 4,331,614). This approach involved the transesterification reaction of a phosphonic acid diaryl ester, a bisphenol, a branching agent (tri or tetra phenol or phosphonic acid ester), and a preferred catalyst (e.g., sodium phenolate) carried out in the melt, usually in an autoclave. Several patents have addressed the use of branching agents in polyphosphonates (see e.g., U.S. Pat. Nos. 2,716,101; 3,326,852; 4,328,174; 4,331,614; 4,374,971; 4,415,719; 5,216,113; 5,334,692; and 4,374,971). These approaches have met with some degree of success, however, the combination of properties exhibited by these polyphosphonates are still not sufficient for general acceptance in the marketplace. For example in branched polyphosphonates, the number average molecular weights as high as 200,000 g/mole are claimed with a minimum requirement of 11,000 g/mole (see e.g., U.S. Pat. No. 4,331,614) with polymer dispersities less than 2.5. Consequently these polyphosphonates exhibited high melt viscosities. This approach was successful in producing high molecular weight polyphosphonates that exhibited improved toughness, but processability was sacrificed. Another disadvantage for this process is that it requires high purity monomers, preferably greater than 99.7% (see e.g., U.S. Pat. No. 4,331,614) that make it expensive. Another shortcoming of both the linear and branched polyphosphonates was the lack of hydrolytic stability and haze.

Recently, the development of a method to produce branched polyphosphonates with a superior combination of properties was disclosed ("Branched Polyphosphonates that Exhibit an Advantageous Combination of Properties, and Methods Related Thereto", 2004 0167284 A1, published Aug. 26, 2004, Ser. No. 10/374,829, filing date Feb. 24, 2003). In practice, these materials are stable for more than 5 hours at 300° C. under vacuum (<0.5 mm Hg) but can experience degradation upon exposure to high temperature (>250° C.) and air, air (oxygen), moisture or combinations thereof. The polyphosphonates are exposed to such conditions not during the final stages of synthesis, but when melt mixing with other polymers or during molding processes. The degradation is manifested by reduction in molecular weight that in turn causes loss of mechanical properties such as strength, modulus and toughness. In addition, the fire resistance is negatively affected by this reduction in molecular weight. As the molecular weight decreases, the melt flow of the material increases so that in a flame, the material propensity to drip increases significantly. Thus, additives that can prevent any unwanted degradation of polyphosphonates during thermal treatment are needed.

A list of patents on both linear and branched polyphosphonates is provided below.

1. U.S. Pat. No. 2,435,252 (1948 A. D. F. Toy, et al., Victor Chemical Works)
2. U.S. Pat. No. 2,682,522 (1954 H. W. Coover, et al., Eastman Kodak)
3. U.S. Pat. No. 2,716,101 (1955 H. W. Coover, et al., Eastman Kodak)
4. U.S. Pat. No. 2,891,915 (1959 W. B. McCormack, et al., DuPont)
5. U.S. Pat. No. 3,326,852 (1967 I. M. Thomas, et al., Owens Illinois, Inc)
6. U.S. Pat. No. 3,719,727 (1973 Y. Masai, et al., Toyo Spinning Co.)
7. U.S. Pat. No. 3,829,405 (1974 S. L. Cohen, et al., Fiber Industries and Celanese Corp)
8. U.S. Pat. No. 3,830,771 (1974 S. L. Cohen, et al., Fiber Industries and Celanese Corp)
9. U.S. Pat. No. 3,925,303 (1975 A. Rio, et al., Rhone-Poulenc)
10. U.S. Pat. No. 3,932,351 (1976 H. L. King, et al., Monsanto)
11. U.S. Pat. No. 4,033,927 (1977 F. H. Borman, et al., General Electric)
12. U.S. Pat. No. 4,152,373 (1979 M. L. Honig, et al., Stauffer Chemical Co.)
13. U.S. Pat. No. 4,223,104 (1980 K. S. Kim, et al., Stauffer Chemical Co.)
14. U.S. Pat. No. 4,229,552 (1980 M. Shiozaki, et al., Nissan Chemical Industries, Ltd.)
15. U.S. Pat. No. 4,322,530 (1982 M. Schmidt, et al., Bayer AG)
16. U.S. Pat. No. 4,331,614 (1982 M. Schmidt, et al., Bayer AG)
17. U.S. Pat. No. 4,332,921 (1982 M. Schmidt, et al., Bayer AG)

18. U.S. Pat. No. 4,401,802 (1983 M. Schmidt, et al., Bayer AG)
19. U.S. Pat. No. 4,408,033 (1983 R. E. Hefner, et al., Dow Chemical Co)
20. U.S. Pat. No. 4,415,719, (1983 M. Schmidt, et al., Bayer AG)
21. U.S. Pat. No. 4,474,937 (1984 S. E. Bales, et al., Dow Chemical Co.)
22. U.S. Pat. No. 4,322,520 (1982, M. Schmidt, et al., Bayer AG)
23. U.S. Pat. No. 4,328,174 (1982, M. Schmidt, et al., Bayer AG)
24. U.S. Pat. No. 4,374,971 (1983, M. Schmidt, et al., Bayer AG)
25. U.S. Pat. No. 4,481,350 (1984, M. Schmidt, et al., Bayer AG)
26. U.S. Pat. No. 4,508,890 (1985, M. Schmidt, et al., Bayer AG)
27. U.S. Pat. No. 4,719,279 (1988, H. Kauth, et al., Bayer AG)
28. U.S. Pat. No. 4,762,905 (1988, M. Schmidt, et al., Bayer AG)
29. U.S. Pat. No. 4,782,123 (1988, H. Kauth, et al., Bayer AG)
30. U.S. Pat. No. 5,334,694 (1994, H. Jung, et al., Bayer AG)

Additives have been designed for use with specific plastics to provide protection from degradation due to exposure to high temperature (>250° C.) and air, air (oxygen), moisture or combinations thereof. A wide variety of additives are commercially available, for example Ultranox Phosphite antioxidants, General Electric Specialty Materials, Morgantown, WVA; Irgafos Phosphites, and Irganox Phenolics, Ciba Specialty Chemicals, USA. However, since polyphosphonates with a desirable combination of properties were heretofor unknown materials, no additives have been specifically designed for use with these polymers. Therefore, it is not obvious which, if any, of the available additives will provide protection to polyphosphonates from degradation due to exposure to high temperature (>250° C.) and air, air (oxygen), moisture or combinations thereof.

SUMMARY OF THE INVENTION

In view of the above, there is a need for specific additives for use with polyphosphonates that prevent degradation from high temperature and air, air, moisture and combinations thereof. Therefore specific additives suitable for use with polyphosphonates, concentration ranges and process for mixing are disclosed herein. The compositions are comprised of specific additives and polyphosphonates that exhibit significant improvements in resistance to degradation from high temperature and air, air, moisture and combinations thereof as compared to the same polyphosphonates without the additives.

Another need is a suitable, practical process to combine the additives and the polyphosphonates to achieve good mixing and stabilization before degradation occurs.

It is another object of the present invention to formulate polymer mixtures or blends comprising these polyphosphonate/additive compositions and commodity or engineering plastics. A polymer mixture or blend comprises at least one polyphosphonate/additive composition of the present invention with at least one other polymer, which may be a commodity or engineering plastic, such as polycarbonate, polyacrylate, polyacrylonitrile, polyester, polyamide, polystyrene (including high impact polystyrene) polyurethane, polyepoxy, poly(acrylonitrile butadiene styrene), polyimide, polyarylate, poly(arylene ether), polyethylene, polypropylene, polyphenylene sulfide, poly(vinyl ester), polyvinyl chloride, bismaleimide polymer, polyanhydride, liquid crystalline polymer, cellulose polymer, or any combination thereof. The polymer mixture or blend may be produced via blending, mixing, or compounding the constituent polymers. Due to the polyphosphonate/additive compositions of the present invention, the resulting polymer mixture or blend exhibits exceptional flame resistance (e.g., higher LOI), heat stability (minimal Tg depression), and processing characteristics (e.g., reduced melt viscosity) and low color.

It is yet another object of the present invention to produce articles of manufacture from these polyphosphonate/additive compositions or from polymer mixture or blend comprising these polyphosphonates/additives compositions and other polymers. The polyphosphonate/additive compositions and polymer mixtures or blends of the present invention can be used as coatings or they can be used to fabricate free-standing films, fibers, foams, molded articles, and fiber reinforced composites.

The above summary of the present invention is not intended to describe each illustrated embodiment or every implementation of the present invention. The detailed description, which follows, particularly exemplifies these embodiments.

DETAILED DESCRIPTION OF EXEMPLARY EMBODIMENTS

The present invention pertains to compositions comprised of specific additives and polyphosphonates that exhibit superior resistance to degradation from high temperature and air, air, moisture and combinations thereof. The compositions also have an advantageous combination of fire resistance, processability, toughness, low color and low haze. The terms "flame retardant", "flame resistant", "fire resistant" or "fire resistance", as used herein, mean that the composition exhibits a limiting oxygen index (LOI) of at least 27. The phrase "superior resistance to degradation", as used herein, means that the composition (i.e. additive and polyphosphonate) exhibits less of a reduction in molecular weight, toughness and has less of a tendency to drip in a flame than the same polyphosphonate without the additive when exposed to high temperature and air, air, moisture and combinations thereof. Molecular weight, as used herein, is determined by relative viscosity. It is well known that relative viscosity is a measurement that is indicative of the molecular weight in a polymer. It is also well known that a reduction in relative viscosity is indicative of a reduction in molecular weight. Reduction in molecular weight causes loss of mechanical properties such as strength and toughness. The term "toughness", as used herein, is determined qualitatively on a molded specimen.

The preferred polyphosphonates, both linear and branched, were prepared according to the published patents numbered 1-30 listed on pages 2 and 3 of this document. The more preferred polyphosphonates were prepared as described in the patent application entitled "Branched Polyphosphonates that Exhibit an Advantageous Combination of Properties, and Methods Related Thereto" (2004 0167284 A1, published Aug. 26, 2004, Ser. No. 10/374,829, filing date Feb. 24, 2003). According to this published patent application, the reaction to prepare the more preferred branched polyphosphonates is conducted at a high temperature in the melt under vacuum. The reaction temperature and pressure are adjusted at several stages during the course of the reaction. A stoichiometric imbalance (e.g., molar ratio) of the phosphonic acid diaryl ester to the bisphenol and the phosphonium catalyst of up to about 20 mole % excess of either the phosphonic acid diaryl ester or the bisphenol can be used to prepare the branched polyphosphonates.

A variety of additives were investigated to improve the stability of the polyphosphonates to degradation from high temperature and air, air, moisture and combinations thereof. Many additives that are reported to provide stability to plastics were investigated. These include sterically hindered amines, isocyanate oligomers and epoxy oligomers none of which provided any improvement. Preferred additives include sterically hindered phenolic antioxidants, hydrolytically stable organophosphites, organophosphite antioxidants, sterically hindered lactone antioxidants and combinations thereof. The preferred additives are listed in Table 1. Of these preferred additives, the most preferred are sterically hindered phenolic antioxidants and

TABLE 1

Preferred Additives for Polyphosphonates

| Chemical Structure | CAS Reg. Num. | Trade Name | Manufacturer |
|---|---|---|---|
| 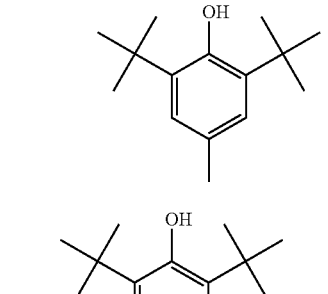 | 10191-41-0 | Irganox E 201 □-Tocopherol | Ciba Specialty Chemicals Various Others |
| 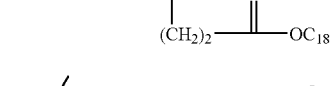 | 128-37-0 | Ionol, Lowinox, Naugard BHT, Dalpac 4, Topanol OC, 2,6-Dirert Butyl-4methylphenol | Shell Great Lakes Uniroyal Hercules ICI Various Others |
| 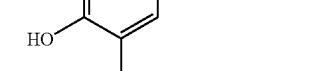 | 2082-79-3 | Irganox 1076 Anox PP18 Lowinox PO35 Naugard 76 | Ciba Specialty Chemicals Great Lakes Uniroyal Various Others |
| 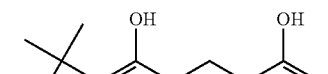 | 12643-61-0 | Irganox 1135 | Ciba Specialty Chemicals |
| 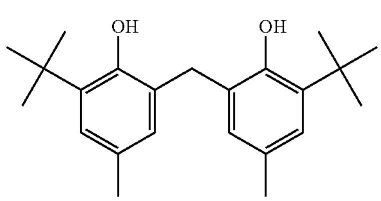 | 119-47-1 | Cyanox 2246 Irganox 2246 Lowinox 22M46 Oxi-Chek 114 Vanox 2246 | Cytec Ciba Specialty Chemicals Great Lakes Ferro Vanderbilt Various Others |
| 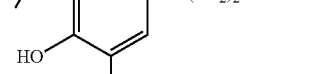 | 35074-77-2 | Irganox 259 | Ciba Specialty Chemicals |

TABLE 1-continued
Preferred Additives for Polyphosphonates
| Chemical Structure | CAS Reg. Num. | Trade Name | Manufacturer |
|---|---|---|---|
| 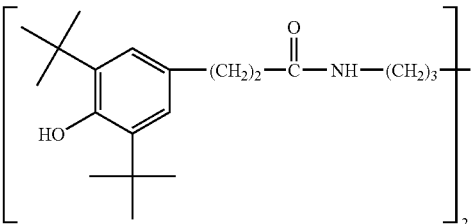 | 23128-74-7 | Irganox 1098 | Ciba Specialty Chemicals |
| 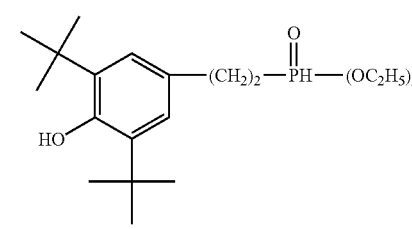 | 976-56-7 | Irganox 1222 | Ciba Specialty Chemicals |
| 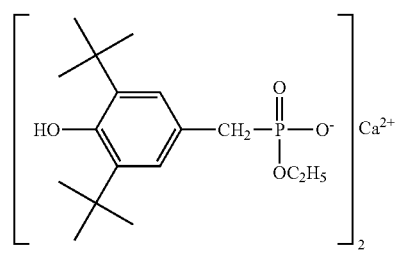 | 65140-91-2 | Irganox 1425 | Ciba Specialty Chemicals |
| 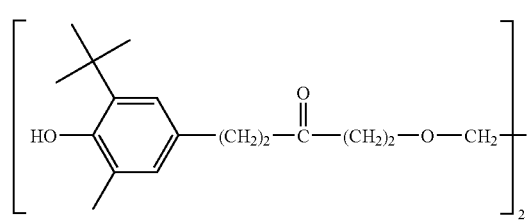 | 36443-68-2 | Irganox 245 | Ciba Specialty Chemicals |
| 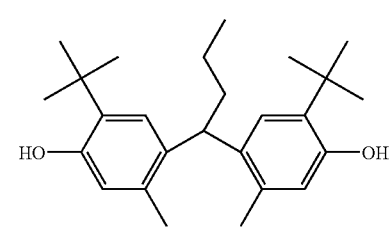 | 85-60-9 | Santowhite Powder | Monsanto |
| 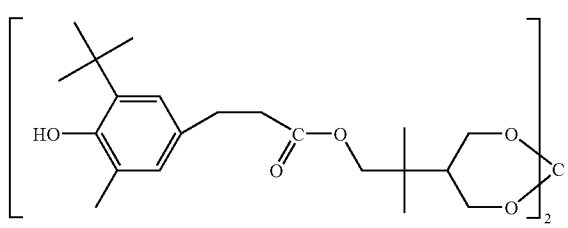 | 90498-90-1 | Sumilizer GA80 | Sumitomo |

TABLE 1-continued

Preferred Additives for Polyphosphonates

| Chemical Structure | CAS Reg. Num. | Trade Name | Manufacturer |
|---|---|---|---|
| [structure: 1,3,5-trimethyl-2,4,6-tris(3,5-di-tert-butyl-4-hydroxybenzyl)benzene] | 1709-70-2 | Ethanox 330<br>Irganox 1330<br>Alvinox 100 | Albemarle<br>3V Sigma<br>Ciba Specialty Chemicals<br>Various Others |
| [structure: Topanol CA - trisphenol] | 1843-03-4 | Topanol CA | ICI |
| [structure: triazine trione with R groups, where R = HO-(3,5-di-tert-butyl-4-hydroxyphenyl)-(CH$_2$)$_2$-C(=O)-O-(CH$_2$)$_2$-] | 34137-09-2 | Goodrite 3125<br>Irganox 3125<br>Vanox SKT | B. F. Goodrich<br>Vanderbilt<br>Ciba Specialty Chemicals |

TABLE 1-continued

Preferred Additives for Polyphosphonates

| Chemical Structure | CAS Reg. Num. | Trade Name | Manufacturer |
|---|---|---|---|
| (triazine trione with R = 3,5-di-tert-butyl-4-hydroxybenzyl) | 27676-62-6 | Goodrite 3114 Irganox 3114 | B. F. Goodrich Ciba Specialty Chemicals |
| (triazine trione with R = tert-butyl-hydroxy-dimethylbenzyl) | 40601-76-1 | Cyanox 1790 Irganox 170 | Cytec Ciba Specialty Chemicals |
| [HO-(3,5-di-tert-butylphenyl)-(CH$_2$)$_2$-C(=O)-O-CH$_2$]$_4$C | 6683-19-8 | Irganox 1010 Anox 20 Adekastab AO-60 | Ciba Specialty Chemicals Great Lakes Ashai Denka Various Others |
| (bis(3-tert-butyl-4-hydroxyphenyl) propane linked via -CH$_2$-C(=O)-CH$_2$-)$_2$ | 6683-19-8 | Hostanox 03 | Clariant |
| (butylated reaction product of p-cresol and dicyclopentadiene) | 31851-03-3 | Wingstay L | Goodyear Various Others |

TABLE 1-continued

Preferred Additives for Polyphosphonates

| Chemical Structure | CAS Reg. Num. | Trade Name | Manufacturer |
|---|---|---|---|
| [structure: 2-methyl-6-(1-methyltetradecyl)phenol with OH, C$_{14}$H$_{29}$] | 134701-20-5 | Irganox 1141 (Blend with Irganox 1076, 1:4) | Ciba Specialty Chemicals |
| [structure: bis-phenol sulfide with tert-butyl groups] | 96-69-5 | Santonox R Santowhite Crystals Irganox 415 Lowinox | Monsanto Great Lakes Ciba Specialty Chemicals Various Others |
| [structure: 2,2'-thiobis(6-tert-butyl-4-methylphenol)] | 90-66-4 | Irganox 1081 | Ciba Specialty Chemicals |
| [structure: 4-methyl-2,6-bis(octylthiomethyl)phenol with SC$_8$H$_{17}$ groups] | 110553-27-0 | Irganox 1520 | Ciba Specialty Chemicals |
| [structure: bis[3-(3,5-di-tert-butyl-4-hydroxyphenyl)propionate] thiodiethylene ester, subscript 2] | 41484-35-9 | Irganox 1034 | Ciba Specialty Chemicals |
| [structure: 2,6-di-tert-butyl-4-(4,6-bis(octylthio)-1,3,5-triazin-2-ylamino)phenol, C$_8$H$_{17}$S and SC$_8$H$_{17}$] | 991-84-4 | Irganox 565 | Ciba Specialty Chemicals |
| [structure: HO-C$_6$H$_4$-NH-C(=O)-C$_{17}$H$_{35}$] | 103-99-1 | Suconox 18 | Bayer |

TABLE 1-continued

Preferred Additives for Polyphosphonates

| Chemical Structure | CAS Reg. Num. | Trade Name | Manufacturer |
|---|---|---|---|
| 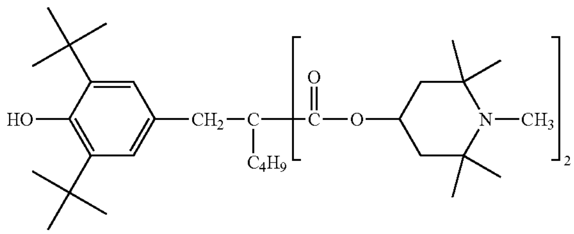 | 63843-89-0 | Tinuvin 144 | Ciba Specialty Chemicals |
| 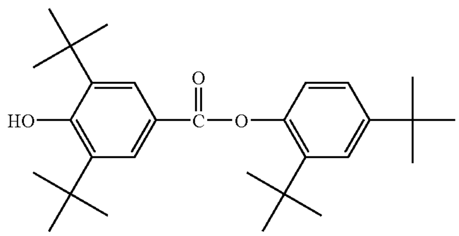 | 4221-80-1 | Tinuvin 120 UV-Chek AM-340 | Ferro Ciba Specialty Chemicals |
| 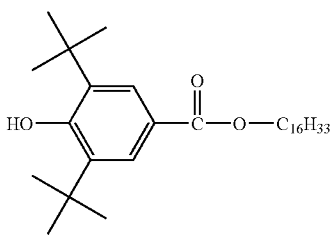 | 67845-93-6 | Cyasoub UV 2908 | Cytec |
| 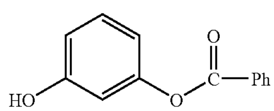 | 136-36-7 | Eastman Inhibitor RMB | Eastman |
| 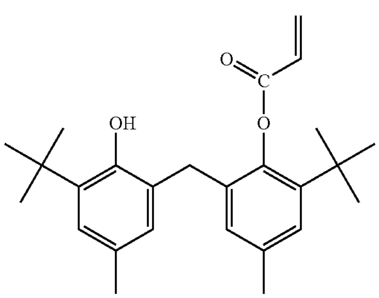 | 61167-58-6 | Sumilizer GM Irganox 3052 | Sumitomo Ciba Specialty Chemicals |
| 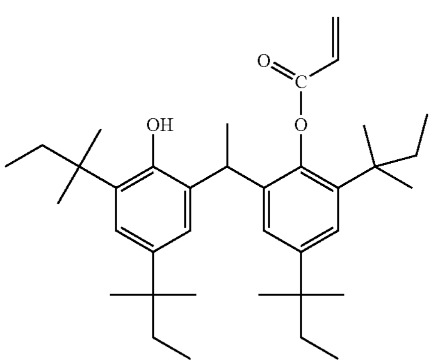 | 128961-68-2 | Sumilizer GS | Sumitomo |

TABLE 1-continued

Preferred Additives for Polyphosphonates

| Chemical Structure | CAS Reg. Num. | Trade Name | Manufacturer |
| --- | --- | --- | --- |
| (di-tert-butyl benzofuranone with dimethylphenyl substituent) | 181314-48-7 | Irganox HP 136 | Ciba Specialty Chemicals |
| HO-N(C$_{18}$H$_{37}$)$_2$ | 143925-92-2 | Irgastab FS 042 | Ciba Specialty Chemicals |
| N-phenyl-2-naphthylamine | 135-88-6 | Vulkanox PBN | Bayer |
| poly(1,2-dihydro-2,2,4-trimethylquinoline) | 26780-96-1 | Flectol H Agerite Resin D | Monsanto Vanderbilt |
| N-isopropyl-N'-phenyl-p-phenylenediamine | 101-72-4 | Vulkanox 4010 NA | Bayer Various Others |
| N-phenyl-1-naphthylamine | 90-30-2 | Vulkanox PAN Nonox AN | Bayer ICI |
| styrenated diphenylamine (octylated) | 68411-46-1 | Irganox 5057 | Ciba Specialty Chemicals |
| (cumyl-substituted diphenylamine) | 10081-67-1 | Naugard 445 | Uniroyal |

TABLE 1-continued

Preferred Additives for Polyphosphonates

| Chemical Structure | CAS Reg. Num. | Trade Name | Manufacturer |
|---|---|---|---|
| (structure) | 118832-72-7 | Irganox L118 | Ciba Specialty Chemicals |
| (structure) | 26523-78-4 | Irgafos TNPP / TNPP / Alkanox TNPP | Great Lakes Clariant / Ciba Specialty Chemicals / Various Others |
| (structure) | 31570-04-4 | Irgafos 168 / Hostanox PAR 240 / Alkanox 240 | Great Lakes Clariant / Ciba Specialty Chemicals / Various Others |
| (structure) | 26741-53-7 | Ultranox 626 | GE Specialty Chemicals / Various Offers |
| (structure) | 80693-00-1 | Mark PEP 36 | Asahi Denka | organophosphite antioxidants used individually or in combination. Sterically hindered phenolic antioxidants, organophosphite antioxidants, hydrolytically stable organophosphites and sterically hindered lactone and amine antioxidants represent broad classes of additives that can encompass many similar chemical structures. As demonstrated herein by using representatives of these classes of additives, it would be anticipated that the invention extends beyond these specific compounds used in the examples to encompass the many compounds that fall within these classes. The chemical structures of most preferred representative antioxidants are presented in Structures of Formula I-V.

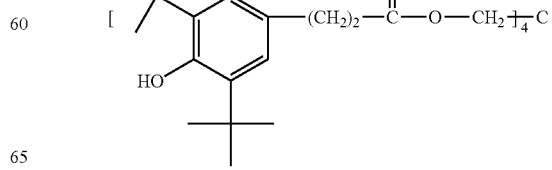

I

-continued

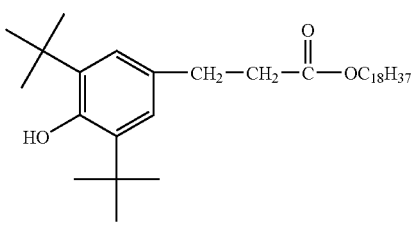

Structure 1. Representative most preferred sterically hindered phenolic antioxidants, (I) tradename Irganox 1010 and (II) tradename Irganox 1076.

The chemical structures of a representative hydrolytically stable organophosphate (III) and an organophosphate antioxidant (IV) are presented in Structure 2.

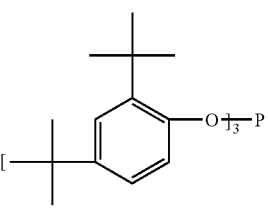

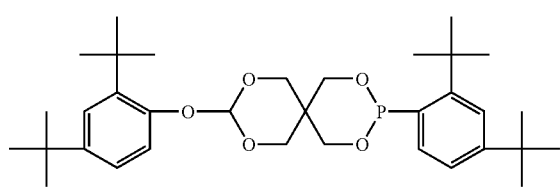

Structure 2. The chemical structures of a representative hydrolytically stable organophosphite (III) tradename Irgafos 168 and a organophosphate antioxidant (IV) tradename Irgafos 126.

The chemical structure of a representative sterically hindered lactone antioxidant is presented in Structure 3.

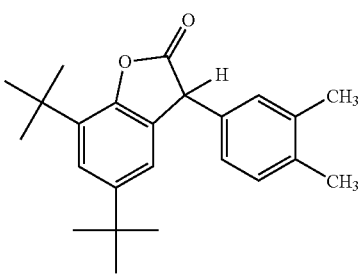

Structure 3. The chemical structure of a representative sterically hindered lactone antioxidant (V) tradename HP-136.

A variety of additive concentrations and combinations were investigated. The best results were obtained with additive concentrations ranging from 0.01 percent by weight to 1.0% by weight. Of this concentration range, 0.05 to 0.5 is preferred and 0.1 to 0.5 is most preferred.

The additives can be introduced into the polyphosphonates by a variety of mixing techniques, all of which are suitable. Preferred techniques include solution mixing whereby the additive is dissolved in a solvent and introduced to the polymer either as a solid or in solution. The most preferred mixing technique is to introduce the additive in solid or liquid form to the molten polyphosphonate under an inert atmosphere or vacuum (i.e. melt mixing).

The resulting compositions comprising the polyphosphonates/additives of the present invention were evaluated for stability to combinations of temperature, moisture and air and compared to the same polyphosphonates without the additives. The compositions comprising the polyphosphonates/additives exhibited superior resistance to degradation as measured by the changes in molecular weight, toughness and tendency to drip when exposed to a flame.

The compositions comprising the polyphosphonates and the additives of the present invention were also used to produce polymer mixtures or blends with commodity and engineering plastics having advantageous characteristics. The term "polymer mixtures or blends", as used herein, refers to a composition that comprises at least one polyphosphonate/additive composition of the present invention and at least one other polymer. There term "other polymer", as used herein, refers to any polymer other than the phosphonate/additive composition of the present invention. These other polymers may be commodity or engineering plastics such as polycarbonate, polyacrylate, polyacrylonitrile, polyester, polyamide, polystyrene (including high impact strength polystyrene), polyurethane, polyepoxy, poly(acrylonitrile butadiene styrene), polyimide, polyarylate, poly(arylene ether), polyethylene, polypropylene, polyphenylene sulfide, poly(vinyl ester), polyvinyl chloride, bismaleimide polymer, polyanhydride, liquid crystalline polymer, cellulose polymer, or any combination thereof (commercially available from, for example, GE Plastics, Pittsfield, Mass.; Rohm & Haas Co., Philadelphia, Pa.; Bayer Corp.—Polymers, Akron, Ohio; Reichold; DuPont; Huntsman LLC, West Deptford, N.J.; BASF Corp., Mount Olive, N.J.; Dow Chemical Co., Midland, Mich.; GE Plastics; DuPont; Bayer; Dupont; ExxonMobil Chemical Corp., Houston, Tex.; ExxonMobil.; Mobay Chemical Corp., Kansas City, Kans.; Goodyear Chemical, Akron, Ohio; BASF Corp.; 3M Corp., St. Paul, Minn.; Solutia, Inc., St. Louis, Mo.; DuPont; and Eastman Chemical Co., Kingsport, Tenn., respectively). The polymer mixtures or blends may be produced via blending, mixing, or compounding the constituent materials.

It is contemplated that polyphosphonates/additive compositions or the polymer mixtures or blends of the present invention may comprise other components, such as fillers, surfactants, organic binders, polymeric binders, crosslinking agents, coupling agents, anti-dripping agents, colorants, inks, dyes, or any combination thereof.

The polyphosphonates/additive compositions or the polymer mixtures or blends of the present invention can be used as coatings or they can be used to fabricate articles, such as free-standing films, fibers, foams, molded articles and fiber reinforced composites. These articles may be well-suited for applications requiring fire resistance.

The polyphosphonates/additive compositions or the polymer mixtures or blends of the present invention are self-extinguishing in that they immediately stop burning when removed from a flame. Any drops produced by melting these polyphosphonates/additive compositions or the polymer mixtures or blends in a flame instantly stop burning and do not propagate fire to any surrounding materials. Moreover, these polyphosphonates/additive compositions or the polymer mixtures or blends do not evolve any noticeable smoke when a flame is applied.

In summary, the polyphosphonates/additive compositions exhibit superior resistance to degradation due to exposure to air, high temperature and air, moisture or combinations thereof. The polyphosphonates/additive compositions and the polymer mixtures or blends of the present invention exhibit superior stability during melt processing. These materials exhibit outstanding flame resistance and a more advantageous combination of heat stability (e.g., Tg), toughness, processability, hydrolytic stability, low color and low haze as compared to the state-of-the-art polyphosphonates without these additives. Such improvements make these materials useful in applications in the automotive and electronic sectors that require outstanding fire resistance, high temperature performance, and low haze.

EXAMPLES

Having generally described the invention, a more complete understanding thereof may be obtained by reference to the following examples that are provided for purposes of illustration only and do not limit the invention.

Example 1

Synthesis of a Branched Polyphosphonate

The branched polyphosphonate was prepared according to the procedure in the published patent application entitled "Branched Polyphosphonates that Exhibit an Advantageous Combination of Properties, and Methods Related Thereto" (2004 0167284 A1, published Aug. 26, 2004, Ser. No. 10/374,829, filing date Feb. 24, 2003).

A 250 mL, three neck round bottom flask equipped with a mechanical stirrer, distillation column (10 cm) filled with hollow glass cylinders, condenser, and vacuum adapter with control valve was flushed with nitrogen for 0.5 hour. Methyldiphenoxy-phosphine oxide (44.57 g, 0.1795 moles), 2,2-bis(4-hydroxyphenyl)propane (bisphenol A), (33.28 g, 0.1458 moles), tetraphenylphosphonium phenolate (0.0127 g, $2.77 \times 10^{-5}$ moles) and 1,1,1-tris(4-hydroxyphenyl)ethane (0.460 g, 0.0015 moles) were placed into the flask and the flask was flushed with nitrogen again. The distillation column was wrapped with heating tape and heated. The reaction vessel was placed in an oil bath and heated to 250° C. until the solids in the flask melted. The reaction mixture was further heated and the vacuum was adjusted at various times during the reaction as indicated in Table 2 below.

TABLE 2

REACTION PARAMETERS FOR EXAMPLE 1

| Time after starting (minutes) | Oil Bath Temp. (° C.) | Column Temp. (° C.) | Vacuum (mm Hg) |
|---|---|---|---|
| 0 | 12 | — | 760 |
| 10 | 153 | 133 | 695 |
| 25 | 252 | 131 | 690 |
| 55 | 250 | 130 | 195 |
| 80 | 250 | 130 | 141 |
| 120 | 250 | 130 | 96 |
| 145 | 250 | 130 | 96 |
| 150 | 250 | 121 | 96 |
| 160 | 250 | 104 | 72 |
| 195 | 250 | 100 | 44 |
| 225 | 250 | 100 | 19 |
| 235 | 250 | 100 | 9 |
| 250 | 250 | 118 | 1.6 |
| 270 | 270 | 107 | 1.5 |
| 295 | 270 | 100 | 1.5 |
| 315 | 305 | 101 | 1.4 |
| 320 | 305 | 127 | 1.4 |
| 340 | 305 | 150 | 1.3 |
| 360 | 305 | 180 | 1.2 |
| 385 | 305 | 180 | 1.2 |
| 390 | Stopped | Stopped | Stopped |

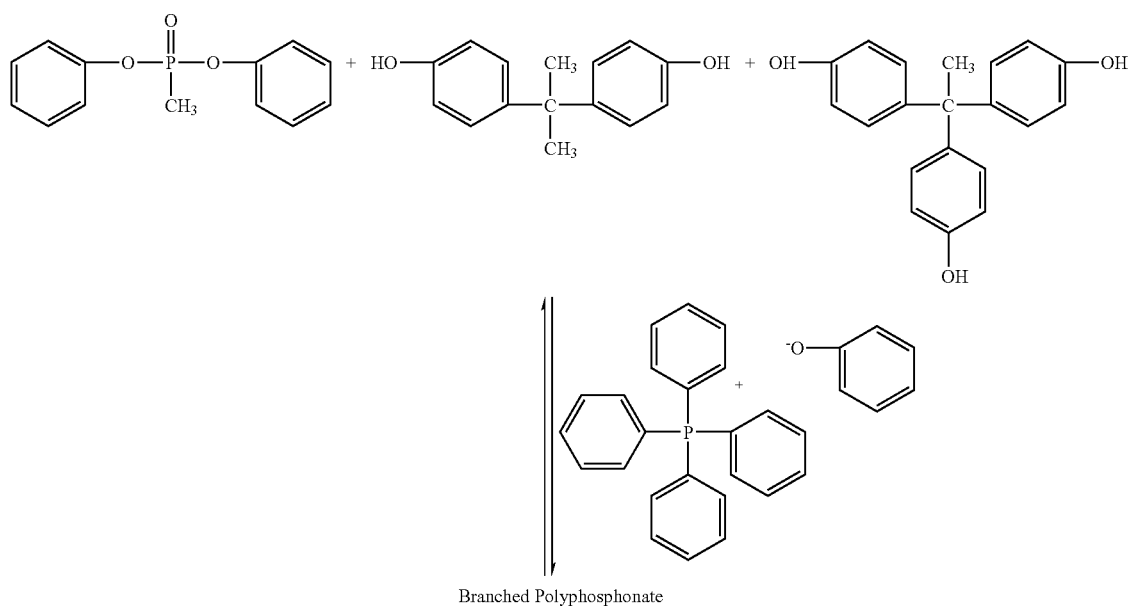

Branched Polyphosphonate

During the course of this reaction 39.21 g of distillate was collected. At the end of the reaction there was a noticeable increase in the viscosity of the polymer melt. The distillation column was removed from the apparatus and additional tetraphenylphosphonium phenolate catalyst (0.0127 g, $4.3 \times 10^{-6}$ moles) was added. Full vacuum was applied and the reaction was heated as indicated in Table 3.

TABLE 3

Reaction Parameters for Example 1 POST REACTION

| Time after starting (minutes) | Oil Bath Temp. (° C.) | Vacuum (mm Hg) |
|---|---|---|
| 0 | 15 | 2.0 |
| 10 | 161 | 1.9 |
| 20 | 221 | 1.7 |
| 25 | 263 | 1.6 |
| 35 | 304 | 1.6 |
| 60 | 305 | 1.5 |
| 90 | 305 | 1.4 |

TABLE 3-continued

Reaction Parameters for Example 1 POST REACTION

| Time after starting (minutes) | Oil Bath Temp. (° C.) | Vacuum (mm Hg) |
|---|---|---|
| 110 | 305 | 1.3 |
| 155 | 305 | 1.1 |
| 170 | 305 | 1.1 |
| 200 | 305 | 1.1 |
| 230 | 305 | 1.1 |
| 250 | 305 | 1.1 |
| 270 | 305 | 1.1 |
| 295 | 305 | 1.0 |
| 320 | 305 | 1.1 |
| 335 | 305 | 1.1 |
| 340 | Stopped | Stopped |

During this post reaction 1.1 g of distillate was collected. Upon cooling, the viscous, pale yellow melt began to solidify. As it solidified, the solid was tough and peeled glass off of the inner walls of the flask. After further cooling to room temperature, the flask was broken to isolate the solid. A 0.5% solution of the polymer in methylene chloride exhibited a relative viscosity of 1.38 at 25° C.

Example 2

Synthesis of a Branched Polyphosphonate

The branched polyphosphonate was prepared according to the procedure in the published patent application entitled "Branched Polyphosphonates that Exhibit an Advantageous Combination of Properties, and Methods Related Thereto" (2004 0167284 A1, published Aug. 26, 2004, Ser. No. 10/374,829, filing date Feb. 24, 2003).

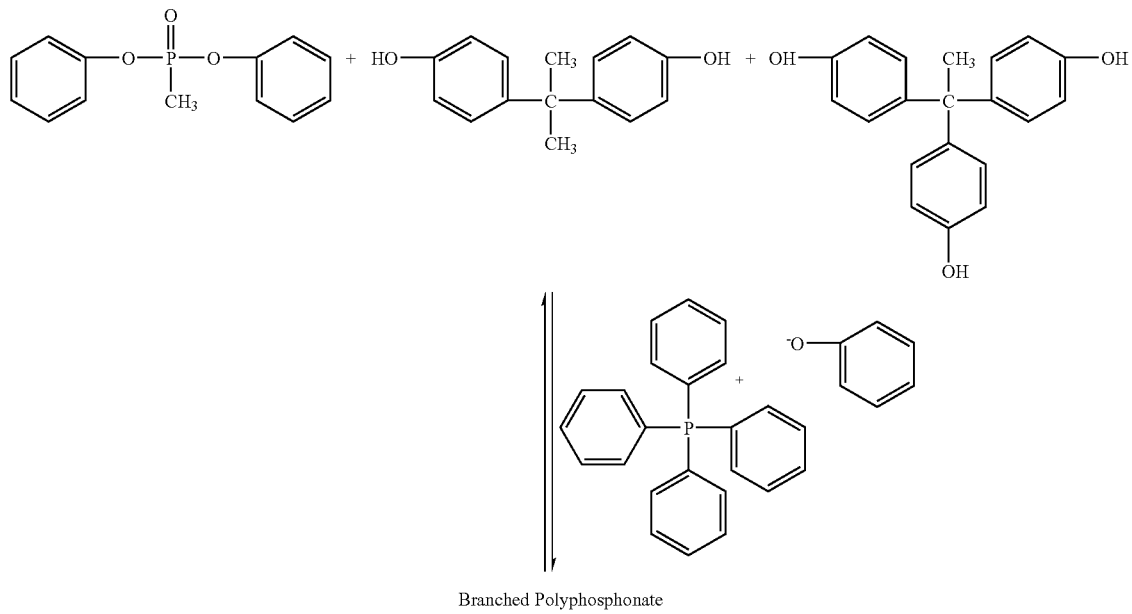

Branched Polyphosphonate

In this example, the reaction was conducted in a pilot plant using methyldiphenoxyphosphine oxide (1400 g)—because this compound is 97.9% pure as determined by HPLC—the precise amount of this compound is actually (1371 g, 5.52 moles), 2,2-bis(4-hydroxyphenyl)propane (bisphenol A), (1308 g, 5.737 moles), tetraphenylphosphonium phenolate (0.451 g, $9.8 \times 10^4$ moles and 1,1,1-tris(4-hydroxyphenyl) ethane (6.4 g, 0.021 moles). The reaction was thermally treated following the protocol described in Table 1 as closely as possible.

Upon cooling, a near colorless melt was obtained. A 0.5% solution of the polymer in methylene chloride exhibited a relative viscosity of 1.4 at 25° C.

Example 3

Analysis of Branched Polyphosphonate Stability

The branched polyphosphonate of Example 1 with a relative viscosity of 1.38 was used in this set of experiments. The polymer without any additive was treated as follows:

1. melt in air/cool in air
2. melt under nitrogen/cool under nitrogen
3. melt and cool under vacuum To melt the polymer, it was heated to approximately 250° C. for about 5 minutes. The relative viscosity was measured after each treatment. The results are presented in Table 3.

TABLE 4

EFFECT OF TREATMENT ON MOLECULAR WEIGHT

| Example | Treatment | $\Box_{rel}$ before | $\Box_{rel}$ after |
|---|---|---|---|
| 1 | melt in air/cool in air | 1.38 | 1.10 |
| 1 | melt under nitrogen/cool under nitrogen | 1.38 | 1.21 |
| 1 | melt and cool under vacuum | 1.38 | 1.38 |

The data in Table 4 indicates that without an additive, the branched polyphosphonate exhibits a reduction in solution viscosity, indicative of molecular weight reduction, upon thermal treatment in air or nitrogen. Since no degradation is noted when treated under vacuum, it appears that the degradation is caused by thermal treatment in the presence of air (oxygen). In the case of the nitrogen treatment, it is likely that some air (oxygen) is also present.

The same experiments were performed on the branched polyphosphonate of Example 2 without any additives. The data is presented in Table 5 and follows the same trend as that for Example 1. It appears that the worst case scenario is to melt and cool the polymer in air.

TABLE 5

EFFECT OF TREATMENT ON MOLECULAR WEIGHT

| Example | Treatment | $\Box_{rel}$ before | $\Box_{rel}$ after |
|---|---|---|---|
| 2 | melt in air/cool in air | 1.40 | 1.15 |
| 2 | melt under nitrogen/cool under nitrogen | 1.40 | 1.22 |
| 2 | melt and cool under vacuum | 1.40 | 1.38 |

Example 4

Analysis of Branched Polyphosphonate of Example 2/Additive Stability

The effect of the treatment in air (worst case scenario) on branched polyphosphonate/additive combinations were performed and compared to the unmodified branched polyphosphonate. The results are presented in Table 6.

TABLE 6

EFFECT OF TREATMENT ON MOLECULAR WEIGHT OF BRANCHED POLYPHOSPHONATE/ADDITIVE COMPOSITIONS

| Additive 1, (wt %) Irganox 1010 | Additive 2, (wt %) Irganox 1076 | Additive 3, wt (%) Irgafos 168 | Total Additive Concentration, % | Treatment | $\Box_{rel}$ after |
|---|---|---|---|---|---|
| I (100) | — | — | 0.1 | Melt under N2 and cool in air | 1.31 |
| I (100) | — | — | 0.2 | Melt under N₂ and cool in air | 1.32 |
| I (100) | — | — | 0.5 | Melt under N2 and cool in air | 1.28 |
| III (100) | — | — | 0.1 | Melt under N2 and cool in air | 1.24 |
| III (100) | — | — | 0.2 | Melt under N₂ and cool in air | 1.28 |
| III (100) | — | — | 0.5 | Melt under N₂ and cool in air | 1.28 |
| IV (100) | — | — | 0.2 | Melt under N₂ and cool in air | 1.16 |
| III (80) | II (20) | — | 0.2 | Melt under N₂ and cool in air | 1.29 |
| III (57) | II (28) | V (15) | 0.2 | Melt under N₂ and cool in air | 1.24 |
| I (50) | III (50) | — | 0.2 | Melt under N₂ and cool in air | 1.22/1.24 |

Data generated on polyphosphonate of Example 2, $\Box_{rel}$ before treatment was 1.40

Stabilizer is added as a solid at RT and the reaction vessel is flushed with nitrogen. The solids are melted, mixed by mechanical stirring and subsequently cooled in air The data in Table 6 shows that the additives improve the resistance of the branched polyphosphonates to degradation from exposure to high temperature and air (oxygen). This is evidenced by the minimal reduction in the relative viscosity. All of the additives provide improvement compared to the neat polymer. Additives I and III seemed to provide the best results as evidenced by only a slight reduction in relative viscosity.

Example 5

Analysis of Branched Polyphosphonate/Additive Stability

The following experiments were performed on the branched polyphosphonate/additive compositions and compared to the unmodified branched polyphosphonate. The additive was mixed in the melt with the branched polyphosphonate of Example 2 under nitrogen and cooled in air. Additives I and III were studied. In both cases, the relative viscosity was initially 1.40 and was only reduced to 1.29/1.28 after introduction of the additive. The samples were then heated to 250° C. in air for 2 minutes and 5 minutes and the relative viscosity measured. The results are presented in Table 7.

TABLE 7

EFFECT OF TREATMENT ON MOLECULAR WEIGHT OF BRANCHED POLYPHOSPHONATE/ADDITIVE COMPOSITIONS

| Additive | Additive Concentration, wt % | Time at 250° C. in air | $\square_{rel}$ after |
|---|---|---|---|
| I (Irganox 1010) | 0.2 | 2 minutes | 1.16 |
| I (Irganox 1010) | 0.2 | 5 minutes | 1.14 |
| III (Irgafos 168) | 0.2 | 2 minutes | 1.22 |
| III (Irgafos 168) | 0.2 | 5 minutes | 1.21 |

Analysis of the data in Table 7 indicates that additive III (hydrolytically stable organophosphate) provides the better stabilization than additive I (sterically hindered phenolic antioxidant).

Example 6

Analysis of the Stability of Branched Polyphosphonate/Additive Compositions Blended with Polycarbonate Blends were also prepared using 60% by weight Macrolon 3103 and 40% by weight of the branched polyphosphonate of Example 2 with additives I and III. As before the additives were added as solids at RT to the reaction vessel and flushed with nitrogen. The materials were melted and stirred under nitrogen and subsequently cooled in air. The samples were then heated to 250° C. in air for 2 minutes and 5 minutes and the relative viscosity measured. The results are presented in Table 8.

TABLE 8

EFFECT OF STABILIZERS ON BRANCHED POLYPHOSPHONATE/POLYCARBONATE BLENDS, HEAT TREATED IN AIR

| Additive 1 (wt %) | Additive 2 (wt %) | Total Additive Concentration, wt % | Time at 250° C. in air | $\square_{rel}$ before heat treatment | $\square_{rel}$ after heat treatment |
|---|---|---|---|---|---|
| I (100) | — | 0.2 | 2 minutes | 1.29 | 1.29 |
| I (100) | — | 0.2 | 5 minutes | 1.29 | 1.24 |
| III (100) | | 0.2 | 2 minutes | 1.27 | 1.26 |
| III (100) | | 0.2 | 5 minutes | 1.27 | 1.26 |
| I (50) | III (50) | 0.4 | 2 minutes | 1.29 | 1.26 |
| I (50) | III (50) | 0.4 | 5 minutes | 1.29 | 1.28 |

Analysis of the data in Table 8 indicates that both additive III (hydrolytically stable organophosphate) and additive I (sterically hindered phenolic antioxidant) provide good stabilization. It also indicates that when both additives are used in combination superior stabilization is realized.

We claim:

1. A method comprising:
introducing at least one additive selected from the group consisting of:

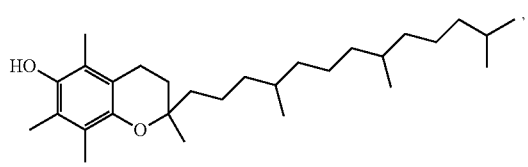

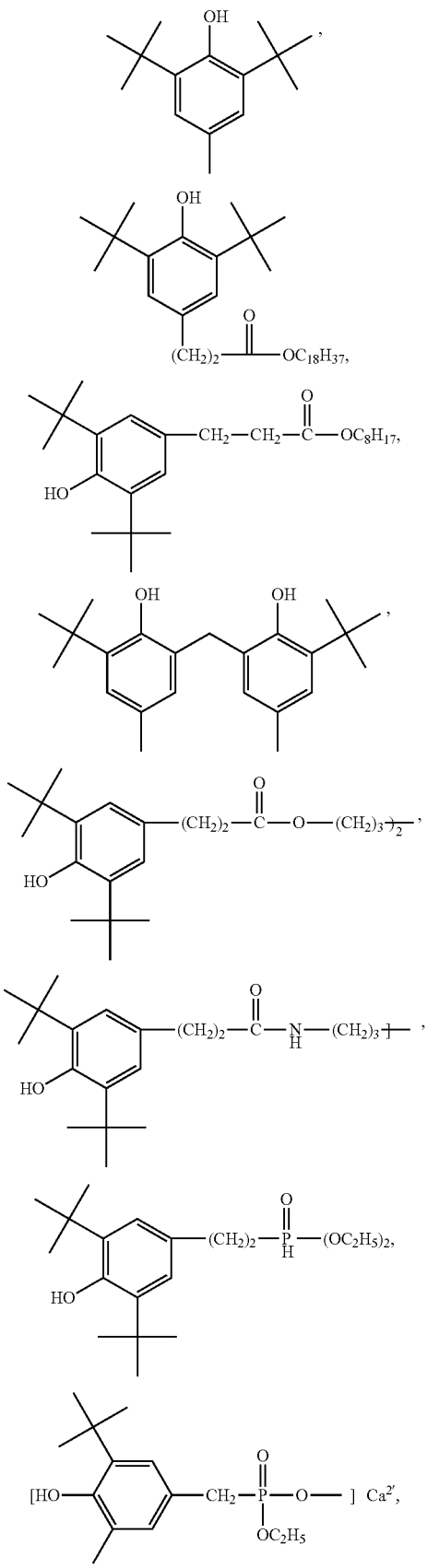

31
-continued
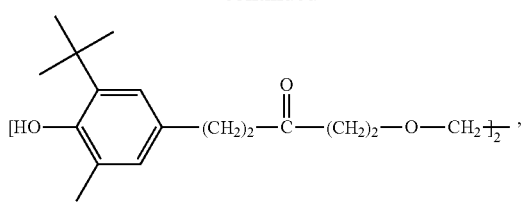
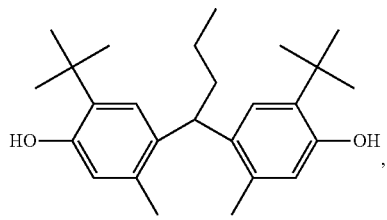
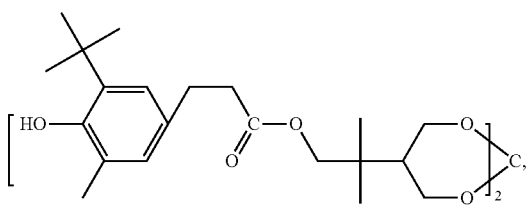
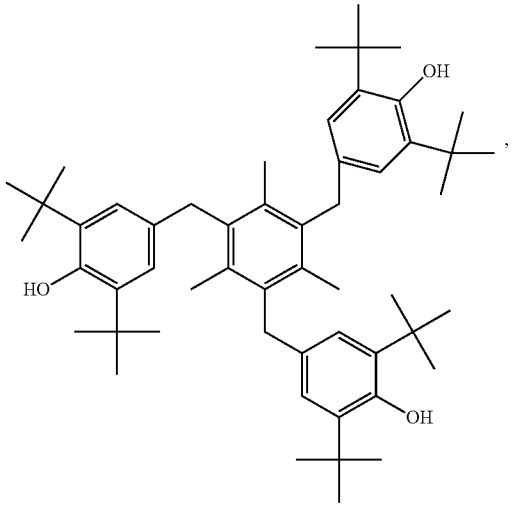
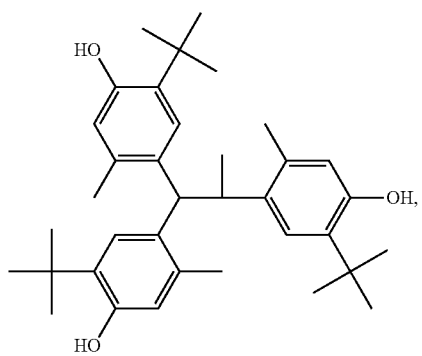
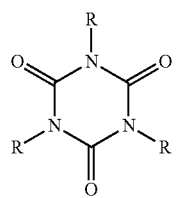
32
-continued
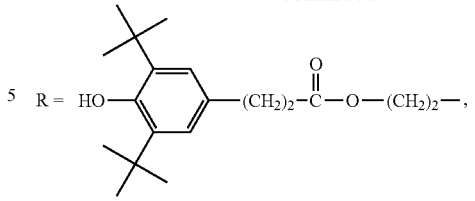
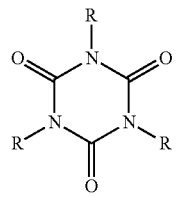
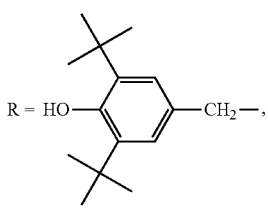
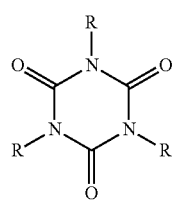
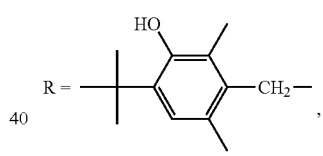
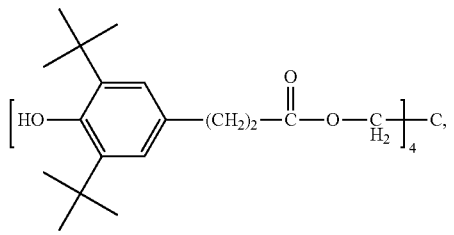
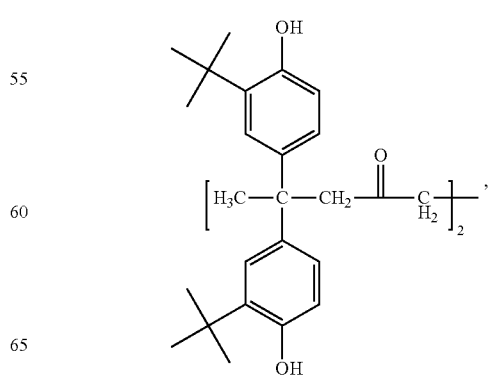

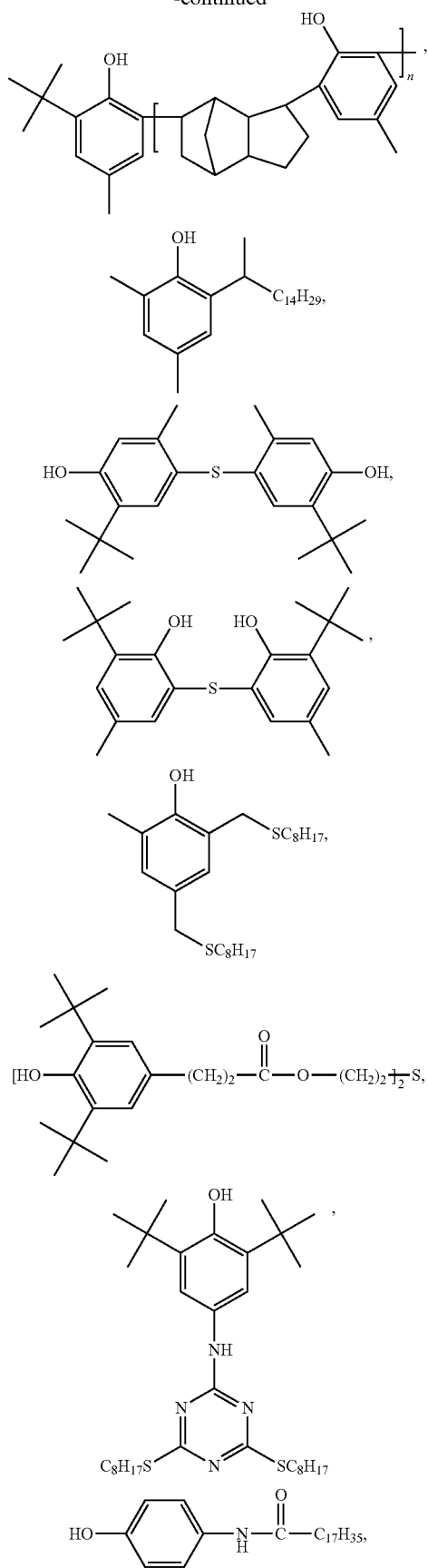
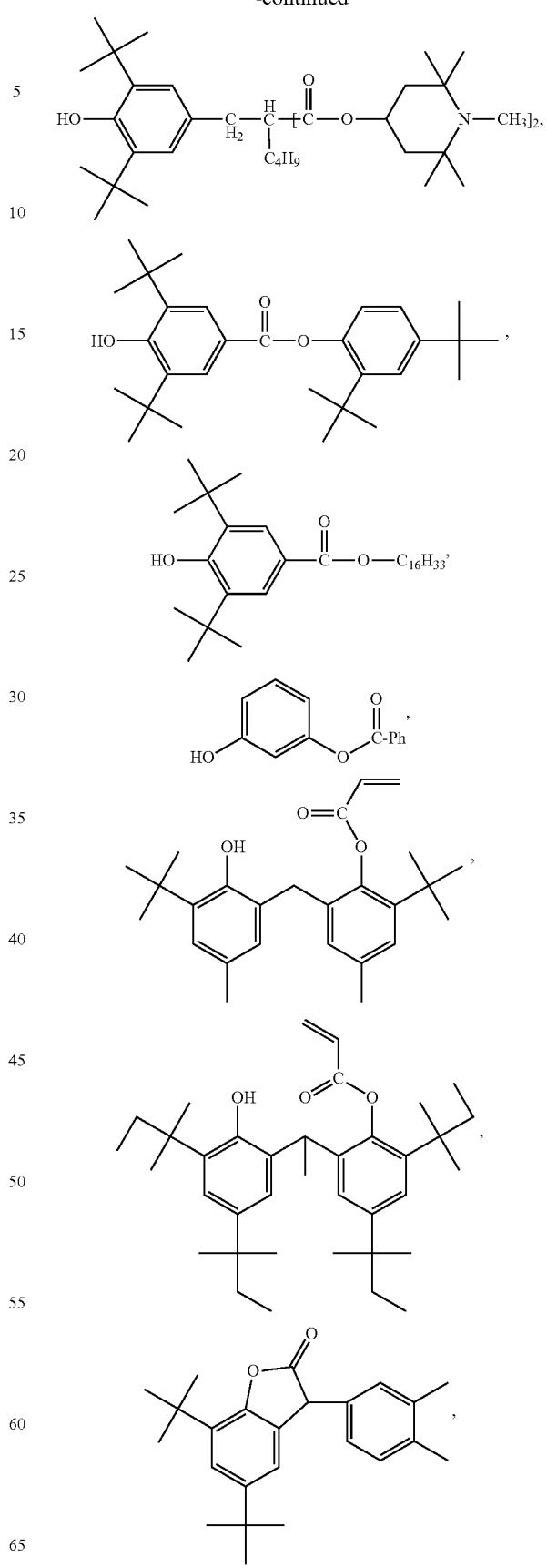

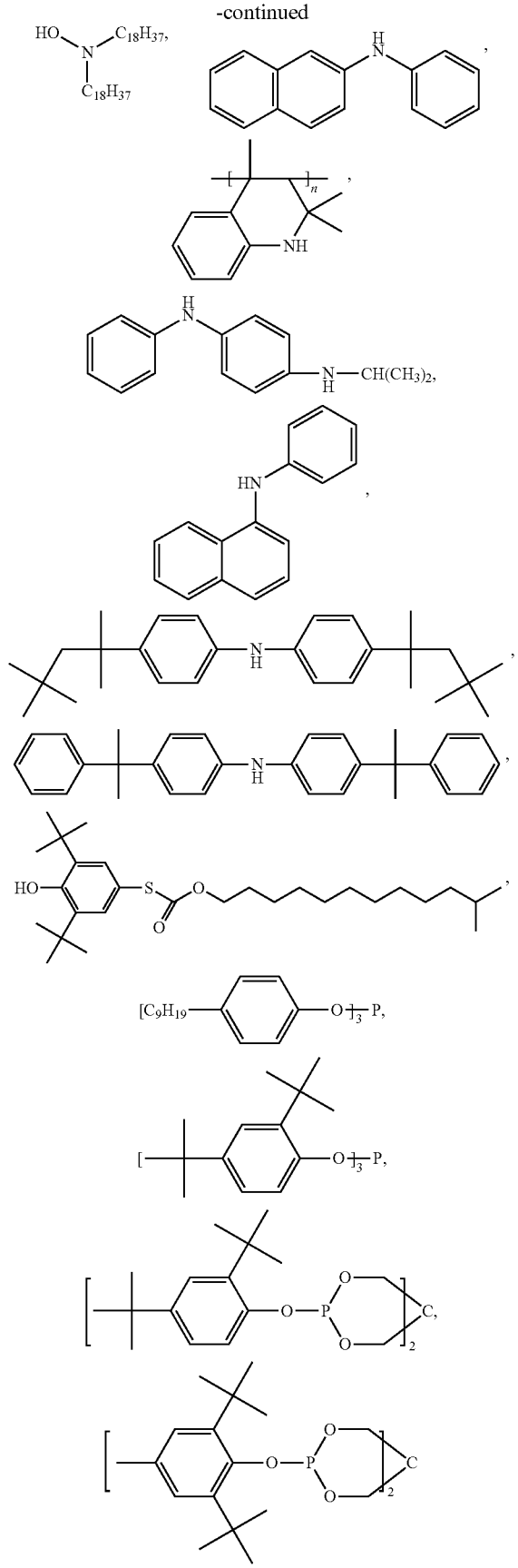

and combinations thereof into one or more high molecular weight polyphosphonates, wherein the one or more high molecular weight polyphosphonates are linear, branched, or combinations thereof.

2. The method of claim 1, wherein introducing comprises melt mixing the one or more high molecular weight polyphosphonates and the at least one additive.

3. The method of claim 2, wherein melt mixing is carried out under vacuum.

4. The method of claim 2, wherein melt mixing is carried out in an inert atmosphere.

5. The method of claim 1, wherein introducing comprises dissolving the at least one additive in a solvent and introducing the dissolved at least one additive and solvent into the one or more high molecular weight polyphosphonates.

6. The method of claim 1, wherein introducing comprises introducing solid at least one additive into the one or more high molecular weight polyphosphonates.

7. The method of claim 1, wherein the at least one additive is selected from:

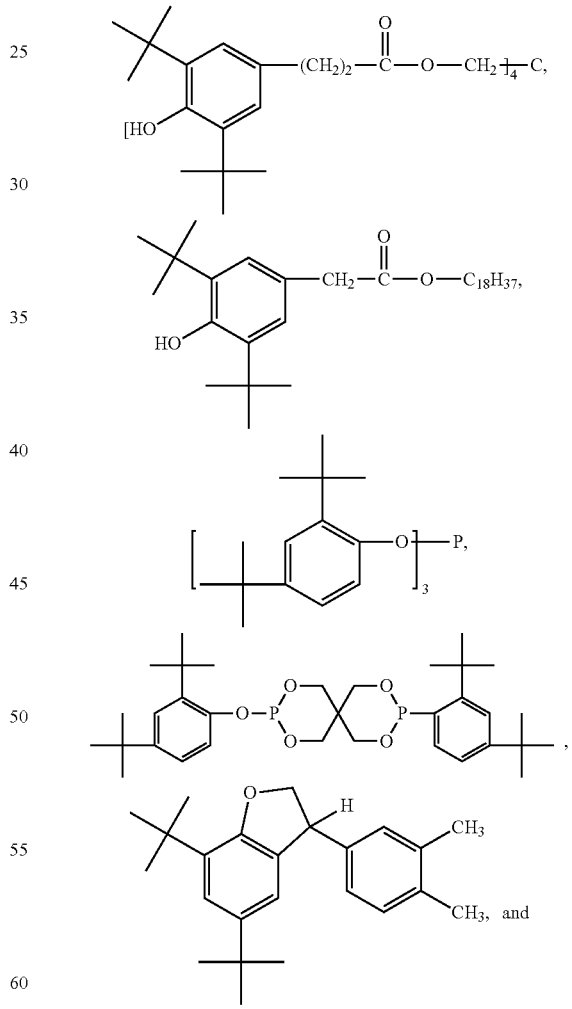

combinations thereof.

8. The method of claim 1, wherein the concentration range of the additives is from about 0.01 to 1.0 percent by weight.

9. The method of claim 1, further comprising introducing one or more other components selected from the group consisting of fillers, surfactants, organic binders, polymeric binders, crosslinking agents, coupling agents, anti-dripping agents, colorants, inks, dyes, and combinations thereof into the polyphosphonate/additive composition.

10. The method of claim 1, further comprising combining the polyphosphonate/additive composition resulting from the method of claim 14 and at least one other polymer.

11. The method claim 10, wherein said at least one other polymer is selected from polycarbonate, polyacrylate, polyacrylonitrile, polyester, polyamide, polystyrene, high impact polystyrene, polyurethane, polyepoxy, poly(acrylonitrile butadiene styrene), polyimide, polyarylate, poly(arylene ether), polyethylene, polypropylene, polyphenylene sulfide, poly(vinyl ester), polyvinyl chloride, bismaleimide polymer, polyanhydride, liquid crystalline polymer, polyether, polyphenylene oxide, cellulose polymer, and combinations thereof.

12. The method of claim 10, wherein said at least one other polymer comprises polycarbonate.

13. The method of claim 10, further comprising introducing one or more other components selected from the group consisting of fillers, surfactants, organic binders, polymeric binders, crosslinking agents, coupling agents, anti-dripping agents, colorants, inks, dyes, and combinations thereof into the polyphosphonate/additive/other polymer composition.

14. The method of claim 1, wherein the one or more high molecular weight polyphosphonates comprises polyphosphonates derived from phosphonic acid diaryl ester and bisphenol.

15. The method of claim 1, wherein the one or more high molecular weight polyphosphonates comprises branched polyphosphonates.

* * * * *